| United States Patent [19] | [11] 3,972,954 |
|---|---|
| Bertus | [45] Aug. 3, 1976 |

[54] PROCESS FOR OXIDATIVE DEHYDROGENATION

[75] Inventor: Brent J. Bertus, Bartlesville, Okla.

[73] Assignee: Phillips Petroleum Company, Bartlesville, Okla.

[22] Filed: Apr. 8, 1974

[21] Appl. No.: 458,721

Related U.S. Application Data

[63] Continuation of Ser. No. 226,299, Feb. 14, 1972, abandoned.

[52] U.S. Cl. ............................ 260/680 E; 252/437; 260/683.3
[51] Int. Cl.$^2$ ........................................... C07C 5/48
[58] Field of Search ...................... 260/680 E, 683.3

[56] References Cited
UNITED STATES PATENTS

| 3,159,688 | 12/1964 | Jennings et al. ................. 260/680 E |
|---|---|---|
| 3,642,930 | 2/1972 | Grasselli et al. ................. 260/680 E |
| 3,678,124 | 7/1972 | Stepanov et al. ................ 260/683.3 |
| 3,737,394 | 6/1973 | Eden ................................... 252/437 |
| 3,755,196 | 8/1973 | Mickelson .......................... 252/437 |
| 3,764,632 | 10/1973 | Takenaka et al. ................ 260/680 E |

*Primary Examiner*—Paul M. Coughlan, Jr.

[57] ABSTRACT

Compositions prepared from (I) an iron group-containing component, such as nickel oxide, (II) a Group VIB-containing component, such as of molybdenum, and (III) a Group VA-containing component, such as a phosphorus, arsenic, or antimony, are effective in a process to convert paraffins or monoolefins to a greater degree of unsaturation.

9 Claims, No Drawings

PROCESS FOR OXIDATIVE DEHYDROGENATION

This application is a continuation of Ser. No. 226,299, filed Feb. 14, 1972, now abandoned.

FIELD OF THE INVENTION

This invention relates to compositions effective as dehydrogenation catalysts. The invention further relates to dehydrogenation processes utilizing the compositions as catalysts.

BACKGROUND OF THE INVENTION

A variety of dehydrogenation catalyst compositions and systems are known. However, the search for better and more effective catalyst compositions, preparations, and processes of utilization continues.

OBJECTS OF THE INVENTION

It is an object of my invention to provide novel compositions useful as catalysts. It is a further object of my invention to provide effective yields of desired products through dehydrogenation processes.

Other aspects, objects, and several advantages of my invention will become apparent to those skilled in the art to which my invention most nearly appertains upon consideration of my disclosure as presented in this specification including my appended claims.

SUMMARY OF THE INVENTION

According to my invention, novel compositions are formed by the combination of (I) an iron group containing component, i.e., a compound of iron, cobalt, or nickel, (II) a Group VIB-containing component, i.e., a compound of chromium, molybdenum, or tungsten, and (III) a Group VA containing component of the third to sixth periods. These compositions, employed as catalyst compositions, exhibit effective properties and abilities to convert, for example, a paraffin to an olefin, such as a butane to butene, or to convert a 1-monoolefin to a diene, such as a butene to corresponding butadiene, or the like, all valuable products for further employments in preparation of such as polybutadiene and other useful polymers, or for dimerization to gasoline components, and the like.

DETAILED DESCRIPTION OF THE INVENTION

Compositions

The compositions of my invention are prepared from a combination of (I) an iron group-containing component of the fourth period of Group VIII of the Periodic Table specifically one or more of iron, cobalt, or nickel, preferably nickel, (II) a Group VIB-containing component, specifically of chromium, molybdenum, or tungsten, preferably molybdenum, and (III) a Group VA-containing component of the third through sixth periods of the Periodic Table, specifically phosphorus, arsenic, antimony, or bismuth, preferably phosphorus. The designations Group VIII, Group VIB, and Group VA refer to the Periodic Table of the Elements as set forth in *Handbook of Chemistry and Physics*, 49th Ed. (1968–1969), The Chemical Rubber Co., Cleveland, Ohio, page B-3.

In my compositions as catalysts according to one aspect of my invention, the relative amounts of each component can vary widely, so long as there is an effective relationship in the final catalyst composition produced, i.e., each component is present in a sufficient weight relationship of one to the other as to provide catalytic effectiveness of the composition combination.

As a working broad range, the (I) iron group component constitutes about 15 to 65 weight percent, the (II) Group VIB component about 10 to 40 weight percent, and the (III) Group VA component about 1 to 25 weight percent, each component being calculated as the element itself.

It presently is most preferred, for conversion and selectivity, that the catalytic compositions reflect a range of (I) about 30 to 45 weight percent for the iron group component, (II) about 15 to 35 weight percent for the Group VIB component, and (III) about 4 to 20 weight percent for the Group VA component, each component again expressive of the element itself.

The total amounts may not equal 100 percent, and need not equal 100 percent, since the elements contained in the compositions can be but are not necessarily in the elemental state. The elements can be combined, for example, with such as oxygen and/or sulfur to form one or more compounds.

The (I) iron group-containing compounds broadly can be employed as a class, including the presently preferred oxides or compounds convertible to the oxides on drying or calcining, such as the hydroxides or nitrates, as well as the halides including fluoride, chloride, bromide, or iodide, the halates including the bromates and other equivalent halates, carboxylates such as acetates, propionates, tartrates, oxalates, and the like, all useful as well as mixtures or combinations thereof. Presently preferred are compounds of nickel.

The (II) Group VB-component containing compounds employed also can be any of the applicable compounds with the qualifications as discussed above for the nickel group components. Presently preferred are the compounds of molybdenum.

The (III) Group VA-component containing compounds can by any applicable compound of a Group VA element of the third through the sixth periods of the Periodic Table, subject to the qualifications as described above for the nickel group component. Presently preferred are phosphorus and antimony containing compounds.

Two or more components from each group can be utilized for my catalyst compositions, and where such are employed, then the total thereof is that reflected in the group component weight relationships expressed.

Substantially, any compound or compounds of the aforementioned elements can be employed to make my compositions, so long as none of the compounds are detrimental or contain detrimental components as to the final catalytic effectiveness of the compositions, and so long as elements other than the designated components and oxygen or sulfur associated therewith as compounds are substantially removed from the final catalyst compositions by appropriate washing or volatilization steps including drying and calcining.

Relatively minor amounts of some elements which are or may be present as trace constituents in compounds or component containing materials being employed, or present in a combined form not completely eliminated on drying and-or calcining, are not unacceptable so long as not detrimental in a sufficient degree as to interfere in the effectiveness of my catalyst compositions.

Any of the known double compounds, such as cobalt ferricyanide, and the like, can be utilized in preparations of compositions according to my invention. Further, compounds containing components from two or more groups as I have set forth also can be utilized, such as nickel orthoarsenate, or iron arsenide, or cobalt-orthophosphate, or the like, such that the resulting composition contains the desired components as I have described.

The compositions can be prepared by any suitable method known to the arts for preparation of such compositions. Methods include coprecipitation from aqueous or organic or combination solutions-dispersions or suspensions, impregnation, dry mixing, or the like, alone or in various combinations. In general, any methods can be utilized which provide catalytic compositions containing effective catalytic amounts of the prescribed components in catalytically effective proportions. It is presently preferred that the final compositions as catalysts have a suitably high surface area so as to permit most effective catalytic operations, and it is presently preferred that the compositions have a catalytical surface area of at least 1 square meter per gram.

One suitable and illustrative method of composition preparation involves dry mixing or admixing in the dry state one or more compounds of one or more components from each group, then adding sufficient water or other convenient diluent or slurry-forming liquid or suspension-forming material so as to make a workable slurry, and intimately admixing the components. The components can be admixed in the dry state, without the addition of a slurry forming material, although a slurry is usually more convenient to handle and assists in providing intimate admixture of the components.

The slurry where utilized, then is dried to form a dried composite, usually at a temperature sufficient to volatize the water or other diluents, such as from about 220° to 450°F. The dry or dried composite is calcined at an elevated temperature, which can be any convenient range, such as from 900° to 1800°F., over a time suitable or convenient. Calcination also provides activation of the compositions as catalysts, and suggested times can range upwards to 24 hours more or less. The activation-calcination step preferably includes exposure of the composite during the step to a molecular-oxygen containing gas such as air.

The compositions can be formed into any conventional shape or structure for utilization. The compositions can be prepared in the form of tablets, extrudates, finely divided powders, agglomerates, and the like, by means known to the arts. For convenience in shaping, such particle forming steps can be conducted prior to the calcination-activation step. However, if desired, the composites, without calcination-activation, or afterwards, can be ground, and the ground composition compacted into form suitable for ultimate employment.

The compositions as catalysts can be prepared with or without a support. Where desired for strength, or for catalyst distribution or dilution in various types of reactors and for various hydrocarbon feedstock purposes, a variety of catalyst supports can be utilized including such as silica, boria, titania, zirconia, various types of alumina, and the like, alone or in combination or in admixture, such as silica-alumina and the like. When a support is utilized, the aforementioned weight ratios of one component to the other are exclusive of such support.

Dehydrogenation Feedstocks

Organic feedstocks of which my compositions can be employed as catalysts in dehydrogenation processes are those feedstreams or feedstocks containing one or more dehydrogenatable organic compounds alone or in admixture, or in diluted form with non-dehydrogenatable material such as oxygen, air, steam, nitrogen, and the like.

Such compounds can be characterized as containing at least one

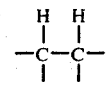

grouping. Compounds to be dehydrogenated typically contain in the range of 2 to 12 carbon atoms per molecule. It certainly is feasible to treat compounds of a dehydrogenatable character containing a greater number of carbon atoms, although such may not be readily commercially available. More specifically, the upper carbon limitation just mentioned does not indicate a limitation on the effectiveness of my compositions as catalysts, nor of processes employing my compositions, but only refer to what may be commercially available in the way of feedstocks.

Particularly applicable for my process employing my compositions as catalysts are the paraffins, including cyclic and acyclic as well, more particularly the acyclic, and also the monoolefins such as the 1-monoolefins, although other monoolefins also can be successfully dehydrogenated to a higher degree of unsaturation. Feedstocks utilized can be as a relatively pure feedstock, i.e., a single compound, or can be as mixed feedstocks available from various refinery streams and containing a variety of components. The compounds to be dehydrogenated can be of branched or of unbranched structure.

The conversion of butane to butenes, butane to butenes and butadienes, isopentane to isoamylenes and isoprene, and butenes to butadiene, presently are considered most advantageous. Representative other feedstocks or feedstock components include ethane, propane, isobutane, pentane, hexane, 2-methyl-hexane, octane, 2,4-dimethyloctane, 2-methylbutene-1, hexene-2, octene-1, 3-methylnonene-4, dodecene-1, and the like.

Dehydrogenation Conditions

In dehydrogenation processes, particularly the oxidative dehydrogenation processes, the hydrocarbon feedstock, together with a molecular-oxygen containing gas, and optionally further together with steam, is formed into an admixture, usually preheated, and contacted with my compositions as catalysts. Any contacting method or reactor known to the catalytic dehydrogenation arts, and employing any mode of contact, such as the presently preferred fixed catalyst bed, as a single bed, or a graded series of beds of differing degree of catalyst activity or contacting temperature, or by any other contacting method such as fluidized beds, and the like.

Hydrocarbon feedstocks can be dehydrogenated with the process using my compositions as catalysts according to my invention at contacting temperatures over a broad range, and utilizing broad contacting pressure and feed rate, hydrocarbon:oxygen ratios, hydrocarbon:steam ratios, employed in the dehydrogenation arts and suitable for the degree or extent of conversion desired.

Suggested hydrocarbon feed rates can range from about 50 to 5000 GHSV, preferably from 200 to 1000 GHSV; suggested contacting temperatures for such processes can range from about 800° to 1300°F., preferably at present from about 1000° to 1200°F. for improved conversion and selectivity; at convenient contacting pressure, such as from about 7 to about 250 psia; and utilizing hydrocarbon:oxygen ratio of about 1:0.1 to about 1:4, presently preferred about 1:0.5 to 1:1.5.

The use of steam frequently is beneficial in dehydrogenation processes for heat transfer purposes to assist in removing heat of reaction. Where steam is so employed, a steam:hydrocarbon ratio of up to about 50:1 can be utilized. Further dilutions than this usually are unnecessary and wasteful of the steam.

The effluent from the reaction zone or zones can be subjected to any suitable separation method so as to isolate and recover desired product or products, to separate unconverted or partially converted feed or components for recycle to the contacting zone or for other use in the modern integrated chemical refinery or petrochemical processing operation which more and more frequently is being termed a petrocomplexity.

My compositions, employed under appropriate conditions as catalysts, have a long active life and seldom need, if ever, to undergo regeneration. However, should regeneration become indicated or is desired, according to operational controls, or because of inactivation possibly attributable to minor amounts of poisons in the feedstocks or introduced inadvertently or for other causes, my catalyst compositions can be readily regenerated. Regeneration can be accomplished by ceasing the flow of feedstock, continuing the flow of oxygen-containing gas, preferably also steam where such is used primarily to maintain suitable temperatures, and otherwise maintaining operating conditions of temperature and the like for a sufficient time to restore substantial activity to the catalyst compositions.

In processes in reactions of my invention, carbon oxides and water are formed either by chemical reactions, or in the case of the water also by condensation of the steam during recovery of the products. Trace amounts of other oxygenated products usually also are formed, such as furan, aldehydes such as acetaldehyde, furfural, minor amounts of acids such as acetic acid, and the like. Some minor amounts of cracking products also may be formed, which may not be undesirable at all, such as butadiene as a by-product of oxidative hydrogenation of isopentane to isoprene. Such products frequently have considerable value in their own right.

EXAMPLES

The following examples serve to illustrate the use of my compositions as catalysts. These examples, and the particular components, species, and conditions as used therein, are intended to be illustrative of my invention and not limitative of the reasonable and proper scope thereof.

In the examples, percent conversion is defined as moles of butene converted/moles of butene in the feed (100). Percent yield is defined as moles of butadiene produced/moles of butene in the feed (100). Percent modivity is defined as a modified selectivity based on analysis of gas phase products for converted hydrocarbons, oxides of carbon and unconverted feed. Conversion and yield are calculated from the same analyses as for modivity. Percent selectivity is defined as moles butadiene produced/moles butene destroyed (100) or yield/conversion.

EXAMPLE I

Catalyst composition No. 1 was prepared according to my invention containing nickel/molybdenum/phosphorus. Nickel oxide, 25 grams, and molybdenum trioxide, 20 grams, were dry mixed, then wetted with 85 weight percent phosphoric acid, 10 grams, and sufficient distilled water to make a conveniently handled paste. The paste was thoroughly mixed, and then dried at about 300°F. for 2 hours. The dried composition was calcined at about 1200°F. in air overnight. The calcined catalyst was ground and screened to about 20–40 mesh. The catalyst contained 38.3 weight percent nickel, 26.1 weight percent molybdenum, 5.3 weight percent phosphorus, each component expressed as the element.

The catalyst so prepared then was used for conversion of butene to butadiene under oxidative dehydrogenation conditions employing a butene feed rate of 300 GHSV, oxygen 264 GHSV, and steam 5780 GHSV. Contacting temperatures and times were varied, as shown in the table below with results as shown.

TABLE I

| Run No. | Temperature °F. | Time Min. | Conversion,% | Yield,% | Modivity,% |
|---|---|---|---|---|---|
| 1 | 1000 | 15 | 38.8 | 28.0 | 72.2 |
| 2 | 1000 | 60 | 36.0 | 27.0 | 74.8 |
| 3 | 1000 | 180 | 35.7 | 26.4 | 74.0 |
| 4 | 900 | 15 | 26.3 | 21.8 | 82.8 |
| 5 | 900 | 60 | 25.5 | 19.7 | 77.4 |
| 6 | 900 | 180 | 24.2 | 17.9 | 74.0 |

The above data reflect the effective conversion and yield of product. Unconverted materials, of course, can be recovered and recycled as necessary or as desired, or employed for other end uses within the petrocomplexity.

EXAMPLE II

Nickel oxide, 25 grams, molybdenum trioxide, 20 grams, and antimony trioxide, 10 grams, were dry mixed, then wetted with distilled water to form a workable paste. The paste was mixed, then dried at 300°F. for 2 hours. The dried composition was calcined at about 1200°F. overnight in air. The resulting composition was ground to 20–40 mesh. Catalyst composition No. 2 contained 35.7 weight percent nickel, 24.3 weight percent molybdenum, 15.2 weight percent antimony, each component expressed as the element.

The so-prepared catalyst then was used for butene conversion employing oxidative dehydrogenation conditions with a butene feed rate of 300 GHSV, oxygen 264 GHSV, steam 5400 GHSV, and employing a contacting temperature of 1000°F. Contacting time was varied, with results as follows:

TABLE II

| Run No. | Time | Conversion,% | Modivity,% | Yield,% |
|---|---|---|---|---|
| 7 | 15 min. | 28.3 | 83.0 | 23.5 |
| 8 | 60 min. | 19.1 | 92.2 | 17.6 |

TABLE II-continued

| Run No. | Time | Conversion,% | Modivity,% | Yield,% |
|---|---|---|---|---|
| 9 | 180 min. | 16.2 | 94.3 | 15.3 |

Data above again reflect effective combination of conversion of modivity obtainable by utilization of catalysts of my invention. In the particular composition employed, it is apparent that shorter contacting times may be preferred.

EXAMPLE III

Further catalysts were prepared according to my invention. Catalyst No. 3 prepared from nickel oxide, 25 grams, molybdenum trioxide, 20 grams, and bismuth nitrate pentahydrate, 20 grams, which components were dry mixed, and otherwise treated and prepared as described in preceding Example II. This catalyst had a composition of 36 weight percent nickel, 24.4 weight percent molybdenum, and 15.8 weight percent bismuth, each component expressed as the element.

Catalyst No. 4 was prepared from the components and with the same composition as described for Catalyst No. 2 in Example II above.

Catalyst No. 5 was prepared from nickel oxide 25 grams, molybdenum trioxide 20 grams, and arsenic trioxide 10 grams, otherwise using the same method of preparation as described in Example II above. This catalyst No. 5 had a composition of 35.7 weight percent nickel, 24.3 weight percent molybdenum, 13.8 weight percent arsenic, each component expressed as the element.

Catalysts 3, 4, and 5, were then employed under conditions for conversion of butane to butene and butadiene, employing oxidative dehydrogenation conditions of butane feed rate 50 GHSV, admixed with oxygen 50 GHSV, and steam 500 GHSV, employing a contacting temperature of 1050°F. The following results were obtained:

TABLE III

| Run No. | Catalyst | Conversion,% | Modivity,% | Yield, % | | |
|---|---|---|---|---|---|---|
| | | | | $C_4H_8$ | $C_4H_6$ | Total |
| 10 | 3 | 10 | 33.6 | 1.7 | 1.6 | 3.3 |
| 11 | 4 | 15 | 23 | 3.6 | 0.3 | 3.9 |
| 12 | 5 | 15.9 | 59 | 6.0 | 3.4 | 9.4 |

The data again reflect effectiveness of compositions prepared according to my invention as catalysts, and effective catalytic conversion of hydrocarbons to products of a greater degree of unsaturation.

Reasonable variations and modifications of my invention are possible while still within the scope of my disclosure, and without departing from the intended scope and spirit thereof, as detailed in my specification and the claims appended.

I claim:

1. An oxidative dehydrogenation process wherein at least one dehydrogenatable monoolefinic hydrocarbon compound containing at least one

grouping is dehydrogenated under oxidative dehydrogenation conditions in admixture with molecular oxygen to products comprising hydrocarbons of a higher degree of unsaturation as compared to said dehydrogenatable monoolefinic hydrocarbon compound, which process comprises
   contacting said dehydrogenatable monoolefinic hydrocarbon compound with a catalyst composition consisting of, exclusive of support, (I) about 15 to 65 weight percent nickel, (II) about 10 to 40 weight percent molybdenum, (III) about 1 to 25 weight percent phosphorus, and (IV) oxygen, or oxygen and sulfur, wherein the weight percent of each of said components is in a ratio of each to the other sufficient to provide catalytic effectiveness for said composition in said oxidative dehydrogenation process.

2. The process according to claim 1 wherein said catalyst composition contains about 30 to 45 weight percent nickel, about 15 to 35 weight percent molybdenum, and about 4 to 20 weight percent phosphorus.

3. The process according to claim 1 wherein said process further employs steam in admixture with said dehydrogenatable monoolefinic hydrocarbon compound and molecular oxygen.

4. The process according to claim 3 wherein said oxidative dehydrogenation conditions further include a contacting temperature of about 800° to 1300°F, a pressure about 7 t0 250 psia, a hydrocarbon:oxygen ratio of about 1:0.1 to 1:4, a steam:hydrocarbon ratio of up to about 50:1, and a hydrocarbon feed rate of about 50 to 5000 GHSV.

5. The process according to claim 4 wherein said contacting temperature is about 1000° to 1200°F., said hydrocarbon:oxygen ratio is about 1:0.5 to 1:1.5, and said hydrocarbon feed rate is about 200 to 1000 GHSV.

6. The process according to claim 4 wherein said dehydrogenatable monoolefinic hydrocarbon compound contains 2 to 12 carbon atoms per molecule.

7. The process according to claim 6 wherein said dehydrogenatable monoolefinic hydrocarbon compound is butene, 2-methylbutene-1, hexene-2, octene-1, 3-methylnonene-4, or dodecene-1.

8. The process according to claim 7 wherein said dehydrogenatable monoolefinic hydrocarbon compound is a butene.

9. The process according to claim 8 wherein said catalyst composition consists of nickel, molybdenum, phosphorus, and oxygen.

* * * * *